United States Patent
Buckingham et al.

(10) Patent No.: US 12,188,912 B2
(45) Date of Patent: *Jan. 7, 2025

(54) CONCURRENT IN-SITU MEASUREMENT OF WIND SPEED AND TRACE GASES ON MOBILE PLATFORMS FOR LOCALIZATION AND QUALIFICATION OF EMISSIONS

(71) Applicant: SeekOps Inc., Austin, TX (US)

(72) Inventors: Stuart Buckingham, Austin, TX (US); Brendan James Smith, Lakeway, TX (US); Victor Alexander Miller, II, Sonoma, CA (US)

(73) Assignee: SeekOps Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,285

(22) Filed: Feb. 15, 2023

(65) Prior Publication Data

US 2023/0194487 A1    Jun. 22, 2023

Related U.S. Application Data

(63) Continuation of application No. 17/127,016, filed on Dec. 18, 2020, now Pat. No. 11,614,430.

(Continued)

(51) Int. Cl.
  *G01W 1/02* (2006.01)
  *B64U 101/00* (2023.01)
  *G01N 33/00* (2006.01)

(52) U.S. Cl.
  CPC .......... *G01N 33/0009* (2013.01); *G01W 1/02* (2013.01); *B64U 2101/00* (2023.01)

(58) Field of Classification Search
  CPC ... G01N 33/0009; B64C 39/024; G01W 1/02; B64U 2101/00
  See application file for complete search history.

(56) References Cited

U.S. PATENT DOCUMENTS 3,780,566 A    12/1973    Smith et al.
4,135,092 A     1/1979    Milly
(Continued)

FOREIGN PATENT DOCUMENTS

AU      3401499 A    11/1999
CN    101470072 A     7/2009
(Continued)

OTHER PUBLICATIONS

Lilian Joly, The evolution of AMULSE (Atmospheric Measurements by Ultra-Light Spectrometer) and its interest in atmospheric applications. Results of the Atmospheric Profiles of Greenhouse gasEs (APOGEE) weather balloon release campaign for satellite retrieval validation, p. 1-28, Sep. 25, 2019, Atmospheric Measurement Techniques Discussion (Joly).

(Continued)

*Primary Examiner* — Manish S Shah
*Assistant Examiner* — Sharad Timilsina
(74) *Attorney, Agent, or Firm* — Command IP LLP; Michael Zarrabian

(57) ABSTRACT

Systems, devices, and methods for an unmanned aerial vehicle (UAV); a trace gas sensor disposed on the UAV, where the gas sensor is configured to measure a gas point concentration; a wind sensor, where the wind sensor is configured to determine a discrete wind vector corresponding to the gas point concentration measurement; and where the discrete wind vector and gas point concentration measurement are acquired substantially concurrently and co-locally.

15 Claims, 11 Drawing Sheets

Related U.S. Application Data

(60) Provisional application No. 62/950,375, filed on Dec. 19, 2019.

(56) References Cited

U.S. PATENT DOCUMENTS

| | | | |
|---|---|---|---|
| 4,233,564 | A | 11/1980 | Kerbel |
| 4,507,558 | A | 3/1985 | Bonne |
| 4,988,833 | A | 1/1991 | Lai |
| 5,047,639 | A | 9/1991 | Wong |
| 5,075,619 | A | 12/1991 | Said |
| 5,173,749 | A | 12/1992 | Tell et al. |
| 5,291,265 | A | 3/1994 | Kebabian |
| 5,317,156 | A | 5/1994 | Cooper et al. |
| 5,822,058 | A | 10/1998 | Adler-Golden et al. |
| 6,064,488 | A | 5/2000 | Brand et al. |
| 6,509,566 | B1 | 1/2003 | Wamsley et al. |
| 6,549,630 | B1 | 4/2003 | Bobisuthi |
| 7,162,933 | B2 | 1/2007 | Thompson et al. |
| 7,800,751 | B1 | 9/2010 | Silver et al. |
| 7,833,480 | B2 | 11/2010 | Blazewicz et al. |
| 8,294,899 | B2 | 10/2012 | Wong |
| 8,451,120 | B2 | 5/2013 | Johnson, Jr. et al. |
| 8,730,461 | B2 | 5/2014 | Andreussi |
| 9,183,371 | B2 | 11/2015 | Narendra et al. |
| 9,183,731 | B1 | 11/2015 | Bokhary |
| 9,235,974 | B2 | 1/2016 | Johnson, Jr. et al. |
| 9,250,175 | B1 | 2/2016 | McManus |
| 9,494,511 | B2 | 11/2016 | Wilkins |
| 9,599,529 | B1 | 3/2017 | Steele et al. |
| 9,599,597 | B1 | 3/2017 | Steele et al. |
| 10,023,323 | B1 | 7/2018 | Roberts et al. |
| 10,031,040 | B1* | 7/2018 | Smith .................. G06T 7/0004 |
| 10,126,200 | B1 | 11/2018 | Steele et al. |
| 10,268,198 | B2 | 4/2019 | Mantripragada et al. |
| 10,325,485 | B1 | 6/2019 | Schuster |
| 10,365,646 | B1 | 7/2019 | Farnsworth et al. |
| 10,429,546 | B1* | 10/2019 | Ulmer .................. G01P 13/00 |
| 10,830,034 | B2 | 11/2020 | Cooley et al. |
| 10,962,437 | B1 | 3/2021 | Nottrott et al. |
| 11,299,268 | B2 | 4/2022 | Christensen et al. |
| 11,519,855 | B2 | 12/2022 | Black et al. |
| 2002/0005955 | A1 | 1/2002 | Kramer et al. |
| 2003/0160174 | A1 | 8/2003 | Grant et al. |
| 2003/0189711 | A1 | 10/2003 | Orr et al. |
| 2003/0230716 | A1 | 12/2003 | Russell et al. |
| 2004/0012787 | A1 | 1/2004 | Galle et al. |
| 2004/0017762 | A1 | 1/2004 | Sogawa et al. |
| 2004/0212804 | A1 | 10/2004 | Neff et al. |
| 2006/0015290 | A1 | 1/2006 | Warburton et al. |
| 2006/0044562 | A1 | 3/2006 | Hagene et al. |
| 2006/0232772 | A1 | 10/2006 | Silver |
| 2006/0234621 | A1 | 10/2006 | Desrochers et al. |
| 2007/0137318 | A1 | 6/2007 | Desrochers et al. |
| 2008/0169934 | A1 | 7/2008 | Lang et al. |
| 2008/0243372 | A1 | 10/2008 | Bodin et al. |
| 2009/0201507 | A1 | 8/2009 | Kluczynski et al. |
| 2009/0263286 | A1 | 10/2009 | Isomura et al. |
| 2009/0326792 | A1 | 12/2009 | McGrath |
| 2010/0004798 | A1 | 1/2010 | Bodin et al. |
| 2010/0140478 | A1 | 6/2010 | Wilson |
| 2010/0147081 | A1 | 6/2010 | Thomas |
| 2011/0074476 | A1 | 3/2011 | Heer et al. |
| 2011/0150035 | A1 | 6/2011 | Hanson et al. |
| 2011/0164251 | A1 | 7/2011 | Richter |
| 2011/0242659 | A1 | 10/2011 | Eckles |
| 2011/0257944 | A1 | 10/2011 | Du et al. |
| 2012/0120397 | A1 | 5/2012 | Furtaw et al. |
| 2013/0044314 | A1 | 2/2013 | Koulikov et al. |
| 2013/0076900 | A1 | 3/2013 | Mrozek et al. |
| 2013/0208262 | A1 | 8/2013 | Andreussi |
| 2014/0172323 | A1 | 6/2014 | Marino |
| 2014/0204382 | A1 | 7/2014 | Christensen |
| 2014/0236390 | A1 | 11/2014 | Mohamadi |
| 2014/0336957 | A1 | 11/2014 | Hanson et al. |
| 2015/0072633 | A1 | 3/2015 | Massarella et al. |
| 2015/0226575 | A1 | 8/2015 | Rambo |
| 2015/0275114 | A1 | 10/2015 | Tumiatti et al. |
| 2015/0295543 | A1 | 10/2015 | Brown et al. |
| 2015/0316473 | A1 | 11/2015 | Kester et al. |
| 2016/0018373 | A1 | 1/2016 | Pagé et al. |
| 2016/0104250 | A1 | 4/2016 | Allen et al. |
| 2016/0161456 | A1 | 6/2016 | Risk et al. |
| 2016/0202225 | A1 | 7/2016 | Feng et al. |
| 2016/0214715 | A1* | 7/2016 | Meffert .................. G01S 17/88 |
| 2016/0307447 | A1 | 10/2016 | Johnson et al. |
| 2016/0357192 | A1 | 12/2016 | McGrew et al. |
| 2017/0003684 | A1 | 1/2017 | Knudsen et al. |
| 2017/0057081 | A1 | 3/2017 | Krohne et al. |
| 2017/0093122 | A1 | 3/2017 | Bean et al. |
| 2017/0097274 | A1 | 4/2017 | Thorpe et al. |
| 2017/0115218 | A1 | 4/2017 | Huang et al. |
| 2017/0134497 | A1 | 5/2017 | Tarter et al. |
| 2017/0158353 | A1 | 6/2017 | Schmick |
| 2017/0199647 | A1 | 7/2017 | Richman et al. |
| 2017/0206648 | A1 | 7/2017 | Marra et al. |
| 2017/0235018 | A1 | 8/2017 | Foster et al. |
| 2017/0307519 | A1 | 10/2017 | Black et al. |
| 2017/0336281 | A1 | 11/2017 | Waxman et al. |
| 2017/0339820 | A1 | 11/2017 | Foster et al. |
| 2018/0023974 | A1 | 1/2018 | Otani et al. |
| 2018/0024091 | A1 | 1/2018 | Wang et al. |
| 2018/0045561 | A1 | 2/2018 | Leen et al. |
| 2018/0045596 | A1 | 2/2018 | Prasad et al. |
| 2018/0050798 | A1 | 2/2018 | Kapuria |
| 2018/0059003 | A1 | 3/2018 | Jourdainne et al. |
| 2018/0067066 | A1 | 3/2018 | Giedd et al. |
| 2018/0109767 | A1 | 4/2018 | Li et al. |
| 2018/0127093 | A1 | 5/2018 | Christensen et al. |
| 2018/0188129 | A1* | 7/2018 | Choudhury ............ G01N 21/85 |
| 2018/0209902 | A1 | 7/2018 | Myshak et al. |
| 2018/0259955 | A1 | 9/2018 | Noto |
| 2018/0266241 | A1 | 9/2018 | Ferguson et al. |
| 2018/0266946 | A1 | 9/2018 | Kotidis et al. |
| 2018/0284088 | A1 | 10/2018 | Verbeck, IV |
| 2018/0292374 | A1* | 10/2018 | Dittberner ............ G05D 1/0088 |
| 2018/0321692 | A1 | 11/2018 | Castillo-Effen et al. |
| 2018/0322699 | A1 | 11/2018 | Gray et al. |
| 2019/0011920 | A1 | 1/2019 | Heinonen et al. |
| 2019/0011935 | A1 | 1/2019 | Ham et al. |
| 2019/0025199 | A1 | 1/2019 | Koulikov |
| 2019/0033194 | A1 | 1/2019 | DeFreez et al. |
| 2019/0049364 | A1 | 2/2019 | Rubin |
| 2019/0077506 | A1 | 3/2019 | Shaw et al. |
| 2019/0086202 | A1 | 3/2019 | Guan et al. |
| 2019/0095687 | A1 | 3/2019 | Shaw et al. |
| 2019/0154874 | A1 | 5/2019 | Shams et al. |
| 2019/0178743 | A1 | 6/2019 | Mcneil |
| 2019/0195789 | A1 | 6/2019 | Pan et al. |
| 2019/0204189 | A1* | 7/2019 | Mohr, Jr. ............... G01N 21/00 |
| 2019/0212419 | A1 | 7/2019 | Jeong et al. |
| 2019/0220019 | A1 | 7/2019 | Tan et al. |
| 2019/0228573 | A1 | 7/2019 | Sen et al. |
| 2019/0234868 | A1 | 8/2019 | Tanomura et al. |
| 2019/0331652 | A1 | 10/2019 | Ba et al. |
| 2020/0065433 | A1 | 2/2020 | Duff et al. |
| 2020/0109976 | A1 | 4/2020 | Ajay et al. |
| 2020/0182779 | A1 | 6/2020 | Kasten et al. |
| 2020/0249092 | A1 | 8/2020 | Podmore et al. |
| 2020/0373172 | A1 | 11/2020 | Suzuki |
| 2020/0400635 | A1 | 12/2020 | Potyrailo et al. |
| 2021/0017926 | A1 | 1/2021 | Alkadi et al. |
| 2021/0109074 | A1 | 4/2021 | Smith et al. |
| 2021/0140934 | A1 | 5/2021 | Smith et al. |
| 2021/0190745 | A1 | 6/2021 | Buckingham et al. |
| 2021/0190918 | A1 | 6/2021 | Li et al. |
| 2021/0199565 | A1 | 7/2021 | John et al. |
| 2021/0247369 | A1 | 8/2021 | Nottrott et al. |
| 2021/0255158 | A1 | 8/2021 | Smith et al. |
| 2021/0300591 | A1 | 9/2021 | Tian |
| 2021/0321174 | A1 | 10/2021 | Sun et al. |
| 2021/0364427 | A1 | 11/2021 | Smith et al. |
| 2021/0382475 | A1 | 12/2021 | Smith et al. |
| 2022/0113290 | A1 | 4/2022 | Smith et al. |
| 2022/0170810 | A1 | 6/2022 | Miller, II et al. |

(56) References Cited

U.S. PATENT DOCUMENTS

| | | |
|---|---|---|
| 2022/0268952 A1 | 8/2022 | Liang et al. |
| 2022/0341806 A1 | 10/2022 | Miller et al. |
| 2023/0194487 A1 | 6/2023 | Buckingham et al. |

FOREIGN PATENT DOCUMENTS

| | | |
|---|---|---|
| CN | 104458588 A | 3/2015 |
| CN | 205749271 U | 11/2016 |
| CN | 106568516 A | 4/2017 |
| CN | 106769977 A | 5/2017 |
| CN | 107703075 A | 2/2018 |
| CN | 109780452 A | 5/2019 |
| CN | 211508182 U | 9/2020 |
| CN | 112213443 A | 1/2021 |
| DE | 29601472 U1 | 5/1996 |
| DE | 69333010 | 4/2004 |
| DE | 102014013822 A1 | 3/2016 |
| EP | 1371962 B1 | 7/2011 |
| EP | 3339855 A1 | 6/2018 |
| FR | 3047073 A1 | 7/2017 |
| FR | 3047073 B1 | 8/2019 |
| GB | 2538563 A | 11/2016 |
| JP | 200975823 A | 4/2009 |
| KR | 20170062813 A | 6/2017 |
| KR | 101770254 B1 | 8/2017 |
| TW | 522226 B | 3/2003 |
| WO | 1999054700 A2 | 10/1999 |
| WO | 02066950 A1 | 8/2002 |
| WO | 2008021311 A2 | 2/2008 |
| WO | 2015073687 A1 | 5/2015 |
| WO | 2016045791 A1 | 3/2016 |
| WO | 2016162673 A1 | 10/2016 |
| WO | 2017069979 A1 | 4/2017 |
| WO | 2018121478 A1 | 7/2018 |
| WO | 2018227153 A1 | 12/2018 |
| WO | 2019246280 A1 | 12/2019 |
| WO | 2020007684 A1 | 1/2020 |
| WO | 2020028353 A1 | 2/2020 |
| WO | 2020086499 A1 | 4/2020 |
| WO | 2020206006 A1 | 10/2020 |
| WO | 2020206008 A1 | 10/2020 |
| WO | 2020206020 A1 | 10/2020 |
| WO | 2021055902 A1 | 3/2021 |
| WO | 2021158916 A1 | 8/2021 |
| WO | 2022093864 A1 | 5/2022 |
| WO | 2022211837 A1 | 10/2022 |

OTHER PUBLICATIONS

U.S. Appl. No. 62/687,147, filed Jun. 19, 2018, Brendan James Smith.

"SAFESITE Multi-Threat Detection System", Jul. 11, 2012 (Jul. 11, 2012), pp. 1-6, XP055245980.

International Search Report and Written Opinion for PCT/US19/38011 mailed Sep. 9, 2019.

International Search Report and Written Opinion for PCT/US19/38015, mailed Oct. 18, 2019.

International Search Report and Written Opinion for PCT/US19/44119, mailed Oct. 17, 2019.

International Search Report and Written Opinion for PCT/US20/26228 mailed Jul. 1, 2020.

International Search Report and Written Opinion for PCT/US20/26232 mailed Jun. 26, 2020.

International Search Report and Written Opinion for PCT/US20/26246 mailed Jun. 29, 2020.

International Search Report and Written Opinion for PCT/US20/51696, mailed Feb. 3, 2021.

International Search Report and Written Opinion for PCT/US2020/044978, mailed Oct. 26, 2020.

International Search Report and Written Opinion for PCT/US2021/016821 mailed Apr. 26, 2021.

International Search Report and Written Opinion for PCT/US2021/024177, mailed Jun. 23, 2021.

International Search Report and Written Opinion for PCT/US2021/056708, mailed Jan. 27, 2022.

International Search Report and Written Opinion for PCT/US21/42061, mailed Nov. 26, 2021.

International Search Report and Written Opinion for PCT/US21/44532, mailed Jan. 11, 2022.

International Search Report and Written Opinion for PCT/US21/56710, mailed Feb. 23, 2022.

International Search Report and Written Opinion for PCT/US22/38951, mailed Nov. 28, 2022.

International Search Report and Written Opinion of PCT/US19/57305, mailed Jan. 2, 2020.

International Search Report and Written Opinion of PCT/US20/54117, mailed Dec. 22, 2020.

Joly, "Atmospheric Measurements by Ultra-Light Spectrometer (AMULSE) Dedicated to Vertical Profile In Situ Measurements of Carbon Dioxide ($CO_2$) Under Weather Balloons: Instrumental Development and Field Application," Sensors 2016, 16, 1609.

Kelly J F et al. "A capillary absorption spectrometer for stable carbon isotope ratio (C/C) analysis in very small samples", Review of Scientific Instruments, American Institute of Physics, 2 Huntington Quadrangle, Melville, NY 11747, vol. 83, No. 2, Feb. 1, 2012 (Feb. 1, 2012), pp. 23101-23101, XP012161835, ISSN: 0034-6748, DOI: 10.1063/1.3680593.

Khan, "Low Power Greenhouse Gas Sensors for Unmanned Aerial Vehicles", Remote Snse. 2012, 4, 1355-1368.

Krings et al., Atmos. Meas. Tech., 11, 721-739, Feb. 7, 2018.

Villa. "An Overview of Small Unmanned Aerial Vehicles for Air Quality Measurements: Present Applications and Future Prospectives". Sensors. Web . Jul. 12, 2016.

White, "Development of an Unmanned Aerial Vehicle for the Measurement of Turbulence in the Atmospheric Boundary Layer", Atmosphere, v.8, issue 10, 195, pp. 1-25.

International Search Report and Written Opinion for PCT/US23/13893, mailed Jun. 30, 2023.

Clilverd, Mark A. et al., Energetic particle injection, acceleration, and loss during the geomagnetic disturbances which upset Galaxy 15, Journal of Geophysical Research, vol. 117, A12213, doi: 10.1029/2012JA018175, 2012, pp. 1-16 (Year:2012).

Kem, Christoph et al., Spatial Distribution of Halogen Oxides in the Plume of Mount Pagan Volcano, Mariana Islands, Geophysical Research Letters 10.1029/2018GL079245, Sep. 27, 2018, pp. 9588-9596 (Year:2018).

Liao, J. et al. Observations of Inorganic bromine(HOBr, BrO, and Br2) speciation at Barrow, Alaska in spring 2009, Journal of Geophysical Research, vol. 117, D00R16, doi:10.1029/2011JD016641, 2012, pp. 1-11 (Year:2012).

Liu, Siwen et al., Development of a UAV-Based System to Monitor Air Quality over an Oil Field, Montana Technological University, Montana tech Library Digital Commons @ Montana Tech Graduate Theses & Non-Theses, Fall 2018, pp. 1-85 (Year:2018).

Miyama, Toru et al., Estimating allowable carbon emission for $CO_2$ concentration stabilization using a GCM-based Earth system model, Geophysical Research Letters, vol. 36,L19709, doi:10.1029/2009GL039678, 2009, pp. 0094-8276 (Year:2009).

Oppenheimer Clive et al., Ultraviolet Sensing of Volcanic Sulfur Emissions, Elements (An Internatioknal Magazine of Mineralogy, Geochemistry, and Petrology), Apr. 2010, vol. 6, pp. 87-92 (Year:2010).

Parazoo, Nicholas C. et al., Interpreting seasonal changes in the carbon balance of southern Amazonia using measurements of $XCO_2$ and chlorophyll fluorescence from Gosat, Geophysical Research Letters, vol. 40.2829-2833, doi: 10.1002/grl.50452, 2013 pp. 0 2829-2833 (Year:2013).

Queiber, Manuel et al., A new frontier in $CO_2$ flux measurements using a highly portable DIAL laser system, Scientific Reports, DOI: 10.1038/srep33834 1, Sep. 22, 2016, pp. 1-13(Year:2016).

Queiber, Manuel et al., Large-area quantification of subaerial $CO_2$ anomalies with portable laser remote sensing and 2d tomography, The Leading Edge Mar. 2018, pp. 306-313 (Year:2018).

(56) References Cited

OTHER PUBLICATIONS

International Search Report and Written Opinion for PCT/US2023/023933 mailed Sep. 26, 2023.
Cabreira et al. "Survey on Coverage Path Planning with Unmanned Aerial Vehicles", published: Drones, published: Jan. 2019, pp. 1-38, year 2019.
International Search Report and Written Opinion for PCT/US23/23905 mailed Oct. 5, 2023.
Tao Lei et al: "Low-power, open-path mobile sensing platform for high—resolution measurements of greenhouse gases and air pollutants", Applied Physics B, Springer Berlin Heidelberg, Berlin/Heidelberg, vol. 119, No. 1, Mar. 10, 2015 (Mar. 10, 2015), pp. 153-164, XP035445836, ISSN: 0946-2171, DOI:10.1007/S00340-015-6069-1 [retrieved on Mar. 10, 2015].
Tarsitano C G et al: Multilaser Herriott Cell for Planetary Tunable Laser Spectrometers', Applied Optics, Optical Society of America, Washington, DC, US, vol. 46, No. 28, Oct. 1, 2007 (Oct. 1, 2007), pp. 6923-6935, XP001508502, ISSN:0003-6935, Doi: 10.1364/AO.46.006923.
Adame J A et al: "Application of cluster analysis to surface ozone, NOand SOdaily patterns in an industrial area in Central-Southern Spain measured with a DOAS system", Science of the Total Environment, Elsevier, Amsterdam, NL, vol. 429, Apr. 11, 2012 (Apr. 11, 2012), pp. 281-291, XP028491183, ISSN: 0048-9697, DOI: 10.1016/J.SCITOTENV.2012.04.032.
Coombes et al, "Optimal Polygon Decomposition for UAV Survey Coverage Path Planning in Wind", published: Jul. 2018, publisher: 'Sensors' (Year:2018).
He et al. "Static Targets' Track Path for UAVs Meeting the Revisit Interval Requirement", published :2013, publisher : IEEE (Year:2013).

\* cited by examiner

CONCURRENT IN-SITU MEASUREMENT OF WIND SPEED AND TRACE GASES ON MOBILE PLATFORMS FOR LOCALIZATION AND QUALIFICATION OF EMISSIONS

CROSS-REFERENCE TO RELATED APPLICATIONS

This application is a continuation of U.S. Non-Provisional patent application Ser. No. 17/127,016, filed Dec. 18, 2020, which claims priority to and the benefit of U.S. Provisional Patent Application No. 62/950,375, filed Dec. 19, 2019, the contents of all of which are hereby incorporated by reference herein for all purposes.

TECHNICAL FIELD

Embodiments relate generally to gas leak detection, and more particularly collecting trace gas measurements onboard an unmanned aerial vehicle (UAV).

SUMMARY

A system embodiment may include: an unmanned aerial vehicle (UAV); a trace gas sensor disposed on the UAV, where the gas sensor may be configured to measure a gas point concentration; and a wind sensor, where the wind sensor may be configured to determine a discrete wind vector corresponding to the gas point concentration measurement; where the discrete wind vector and gas point concentration measurement are acquired substantially concurrently and co-locally.

In additional system embodiments, the wind sensor may be a wind lidar. In additional system embodiments, the wind sensor may be an ultrasonic sensor. In additional system embodiments, the wind sensor may be disposed on the UAV. In additional system embodiments, the wind sensor may be disposed at a fixed location distal from the UAV.

Additional system embodiments may include: a ground control system (GCS) in communication with the UAV, where the GCS may be configured to transmit a wireless signal to guide the UAV through a flight plan for gas leak detection.

A method embodiment may include: measuring, by at least one trace gas sensor disposed on an unmanned aerial vehicle (UAV), a plurality of gas point concentrations; measuring, by at least one wind sensor, a plurality of discrete wind vectors, where each measured discrete wind vector corresponds to a measured gas point concentration; detecting, by a processor of the UAV in communication with the at least one trace gas sensor and the at least one wind sensor, an elevated trace gas concentration; and sending, by the processor of the UAV, a signal to a ground control system (GCS) indicating the detected elevated trace gas concentration.

In additional method embodiments, each of the measured gas point concentrations and corresponding discrete wind vectors are part of a flight plan flown by the UAV. In additional method embodiments, the flight plan flown by the UAV may be downstream of an infrastructure site.

Additional method embodiments may include: sending, by the GCS, a signal to the processor of the UAV to fly a flight plan to capture a cross section of a gas plume based on the detected elevated trace gas concentration. Additional method embodiments may include: determining, by the processor the UAV, a leak rate of the gas plume based on measured gas point concentration and discrete wind vectors over the flight plan.

In additional method embodiments, determining the leak rate of the gas plume further comprises: determining a surface integral on the flux plane; and determining a flux rate by multiplying the determined surface integral by a freestream velocity, where the freestream velocity comprises a velocity with which the flux plane may be moving through the plume.

Additional method embodiments may include: localizing, by the processor of the UAV, the gas leak based on the determined flux rate. In additional method embodiments, localizing the gas leak further comprises back-calculating gas trajectories using a time history of the measured wind vectors, one or more stability characteristics of the atmospheric boundary layer, and a surface roughness of the surrounding area. In additional method embodiments, determining a surface roughness of the surrounding area comprises using at least one of: a gaussian model with free parameters directly related to surface roughness, a direct measurement of near wall speed, and a measured turbulence spectrum.

Another system embodiment may include: a processor of the UAV having addressable memory, where the processor may be in communicate with at least one trace gas sensor and at least one wind sensor, and where the processor of the UAV may be configured to: receive a measurement from the at least one trace gas sensor disposed on an unmanned aerial vehicle (UAV) of a plurality of gas point concentrations; receive a measurement from the at least one wind sensor of a plurality of discrete wind vectors, where each measured discrete wind vector corresponds to a measured gas point concentration; detect an elevated trace gas concentration based on the received measurement from the at least one trace gas sensor; and fly a flight plan to capture a cross section of a gas plume based on the detected elevated trace gas concentration; where the discrete wind vector and gas point concentration measurement are acquired substantially concurrently and co-locally.

In additional system embodiments, the processor may be further configured to: determine a leak rate of the gas plume based on measured gas point concentration and discrete wind vectors over the flight plan, where determining the leak rate of the gas plume further comprises: determining a surface integral on the flux plane; and determining a flux rate by multiplying the determined surface integral by a freestream velocity, where the freestream velocity comprises a velocity with which the flux plane may be moving through the plume.

In additional system embodiments, the processor may be further configured to localize the gas leak based on the determined flux rate. In additional system embodiments, localizing the gas leak further comprises back-calculating gas trajectories using a time history of the measured wind vectors, one or more stability characteristics of the atmospheric boundary layer, and a surface roughness of the surrounding area. In additional system embodiments, determining a surface roughness of the surrounding area comprises using at least one of: a gaussian model with free parameters directly related to surface roughness, a direct measurement of near wall speed, and a measured turbulence spectrum.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which.

DETAILED DESCRIPTION

Figure 1:
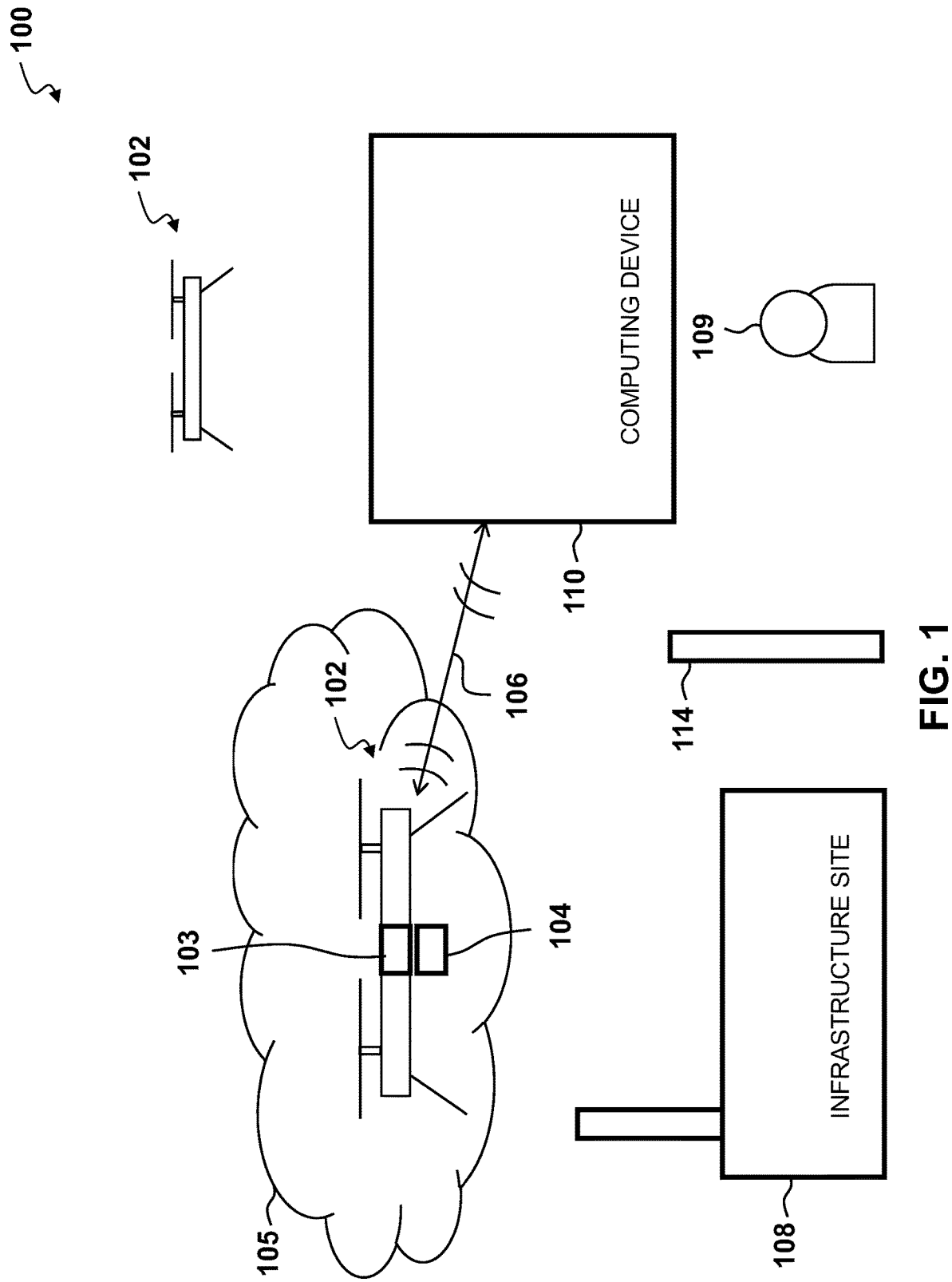
FIG. 1 depicts a system for localizing and quantifying a gas leak.

With respect to FIG. 1, a system 100 allows for the collection of concurrent wind speed and trace gas measurements with a wind sensor 103 and a gas sensor 104 onboard an unmanned aerial vehicle (UAV) 102 to accurately and precisely localize and quantify trace gas emissions. Generally speaking, computer-generated models for extrapolating wind speed measurements taken from the ground level may be highly uncertain in terms of the localization and quantification of trace gases in the atmosphere. The disclosed system 100 provides for associating each gas concentration measurement at a point with a discrete wind vector. More specifically, the association of each gas concentration measurement with a discrete wind vector may be acquired concurrently and co-locally. In other words, they may be acquired at the same time and the same location. For example, a gas concentration and wind speed may be detected at a location $x_1$ and at a time $t_1$ and a second gas concentration and wind speed may be detected at a different location $x_2$ and at a different time $t_2$, and so forth. The location and time coordinates $[x_1, t_1], [x_2, t_2], \ldots [x_n, t_n]$ may then provide for accurate wind and gas concentration gradients for locating and quantifying trace gas leaks, as well as for testing of models to high degrees of accuracy. The system 100, therefore, reduces model-derived uncertainties when calculating trace gas emission sources and trace gas emission rates, leading to enhanced leak detection, localization, and quantification capabilities.

In one embodiment, the UAV 102 may be controlled remotely by an operator 109 operating a computing device 110, such as a ground control system (GCS), cloud server, or the like. The computing device 110 may transmit a wireless signal, such as a radio frequency (RF) signal 106 to guide the UAV 102 through a flight plan for possible leak detection. For example, the computing device 110 may guide the UAV 102 through a possible gas leak site, such as a gas plume 105 associated with an infrastructure site 108. The wind sensor 103 and gas sensor 104 onboard the UAV 102 may collect concurrent wind speed and trace gas measurements.

In some embodiments, the wind sensor 103 may be a wind LIDAR sensor, an ultrasonic sensor, or the like. In some embodiments, the wind sensor 103 may be attached to the UAV 102. In other embodiments, the wind sensor 103 may be attached at a fixed location. In some embodiments, the gas sensor 104 may be attached to the UAV 102. In other embodiments, the gas sensor 104 may attached at a fixed location 114. Any combination of wind sensor 103 and gas sensor 104 may be attached to the UAV 102, another UAV 112, and/or a fixed location 114.

Figure 2:
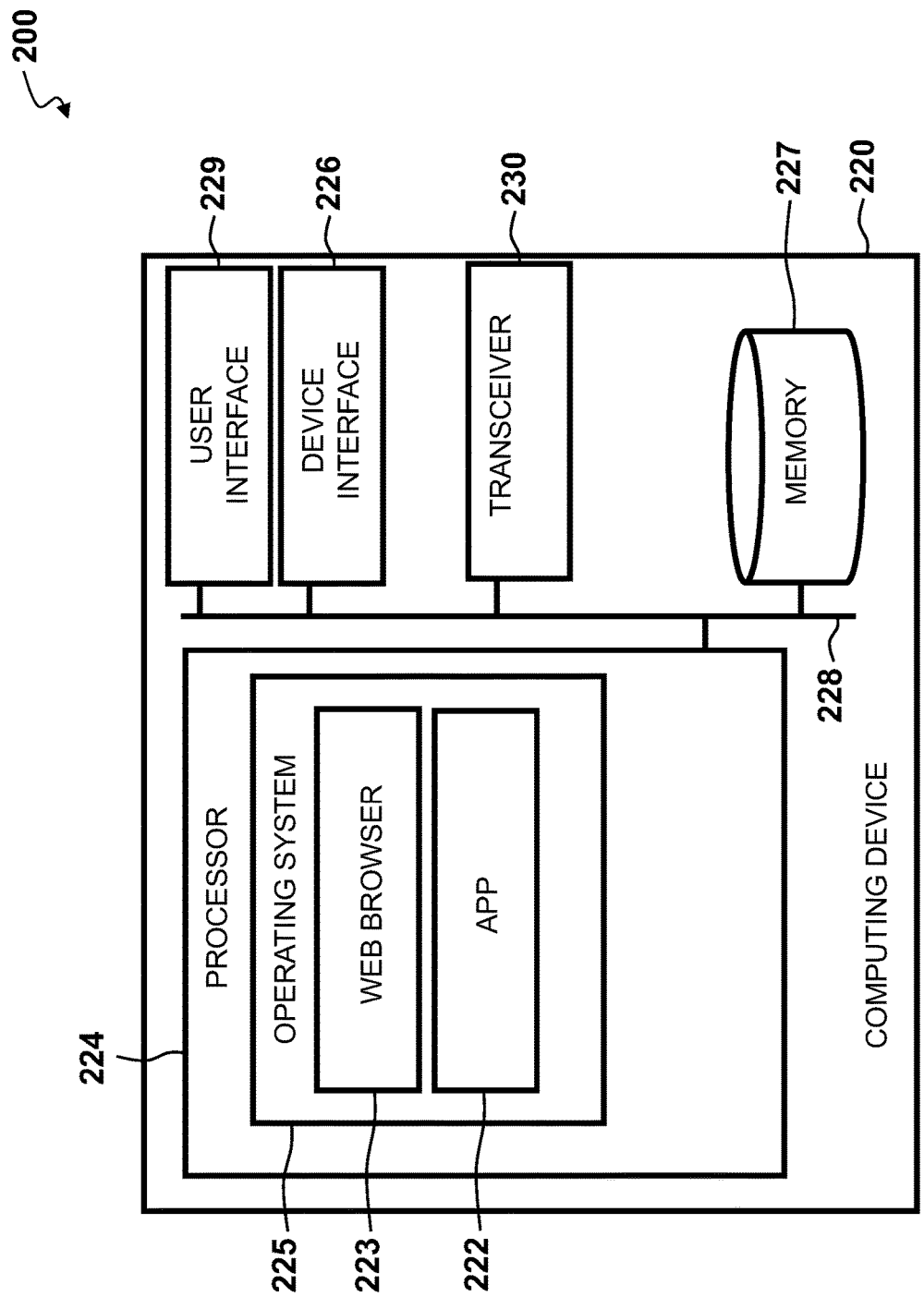
FIG. 2 illustrates an example top-level functional block diagram of a computing device embodiment associated with an unmanned aerial vehicle.

In one embodiment, and with respect to FIG. 2, the UAV 102 may have an onboard computing device 220 in communication with the wind sensor 103 and/or gas sensor 104. FIG. 2 illustrates an example of a top-level functional block diagram of a computing device embodiment 200, where the example operating environment is shown as computing device 220 comprising a processor 224, such as a central processing unit (CPU), addressable memory 227, an external device interface 226, e.g., an optional universal serial bus port and related processing, and/or an Ethernet port and related processing, and an optional user interface 229, e.g., an array of status lights and one or more toggle switches, and/or a display, and/or a keyboard and/or a pointer-mouse system and/or a touch screen. Optionally, the addressable memory may, for example, be: flash memory, eprom, and/or a disk drive or other hard drive. These elements may be in communication with one another via a data bus 228. In some embodiments, via an operating system 225 such as one supporting a web browser 223 and applications 222, the processor 224 may be configured to execute steps of a process establishing a communication channel and processing according to the embodiments described above. The computing device 220 further comprises a transceiver 230 for transmitting and receiving wireless signals, such as RF signal 106 for communication with the remote computing device 110.

Figure 3:
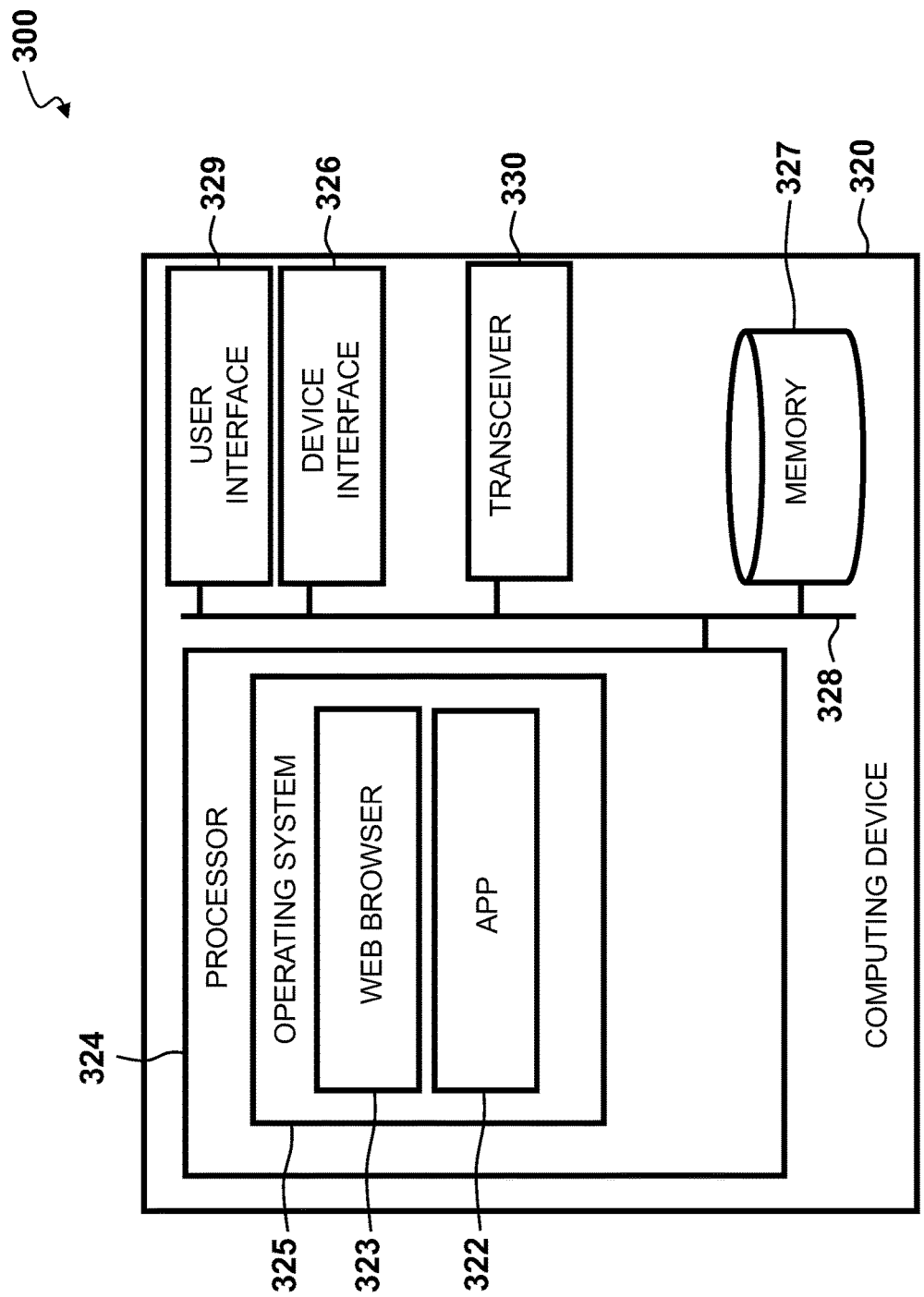
FIG. 3 illustrates an example top-level functional block diagram of a computing device embodiment.

With respect to FIG. 3, an example of a top-level functional block diagram of a computing device embodiment 300 is illustrated. The example operating environment is shown as computing device 320, such as computing device 110 of FIG. 1, comprising a processor 324, such as a central processing unit (CPU), addressable memory 327, an external device interface 326, e.g., an optional universal serial bus port and related processing, and/or an Ethernet port and related processing, and an optional user interface 329, e.g., an array of status lights and one or more toggle switches, and/or a display, and/or a keyboard and/or a pointer-mouse system and/or a touch screen. Optionally, the addressable memory may, for example, be: flash memory, eprom, and/or a disk drive or other hard drive. These elements may be in communication with one another via a data bus 328. In some embodiments, via an operating system 325 such as one supporting a web browser 323 and applications 322, the processor 324 may be configured to execute steps of a process establishing a communication channel and processing according to the embodiments described above. The computing device 320 further comprises a transceiver 330 for transmitting and receiving wireless signals, such as RF signal 106 for communication with the computing device 110.

Figure 4:
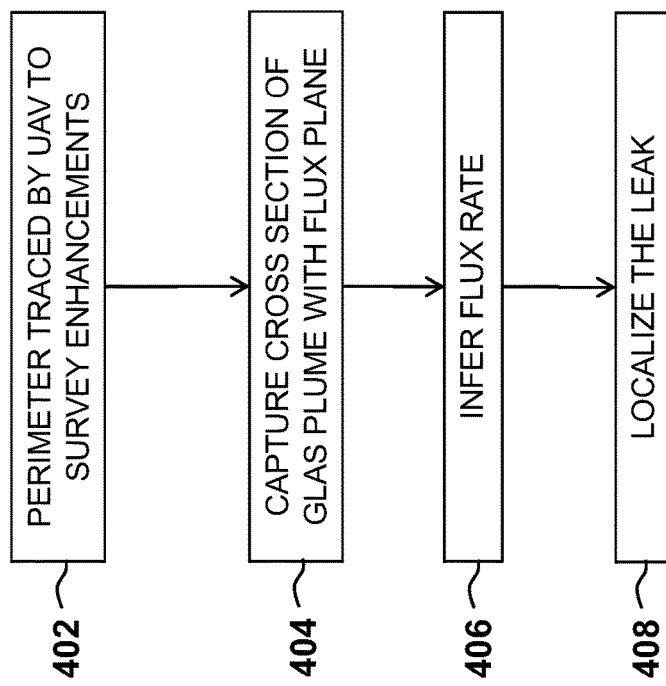
FIG. 4 shows a block diagram and process for implementing an embodiment of the system and process.

With respect to FIG. 4, a process 400 for detecting, localizing, and quantifying trace gas emissions with the collection of concurrent wind speed and trace gas measurements with the sensors 103, 104 shown in FIG. 1 is illustrated. At step 402, a perimeter is flown by the UAV 102 of FIG. 1 downstream of an infrastructure site of interest, such as infrastructure site 108 of FIG. 1. The gas sensor 104 of FIG. 1 onboard the UAV 102 of FIG. 1 surveys for elevated gas concentrations or "enhancements." At step 404, if enhancements are detected via the gas sensor 104 onboard UAV 102, the processor 224 of FIG. 2 of computing device 220 of FIG. 2 may cause the transceiver 220 of FIG. 2 to send the RF signal 106 of FIG. 1 to the computing device 320 of FIG. 3 indicating that the enhancements have been detected. As a result, a flux plane may then be flown to capture the cross section of the gas plume, such as gas plume 105 of FIG. 1 leaking from the infrastructure, such as infrastructure site 108 of FIG. 1.

Provided the flux plane captures the entire extent of the plume 105, the leak rate may be inferred by taking a surface integral on the flux plane, and multiplying the result of the surface integral by the freestream velocity (i.e., the velocity with which the flux plane is moving through the plume 105) to yield a flux rate, as shown in step 406. At step 408, the leak is localized by the processor 324 of FIG. 3 back-calculating the gas trajectories using the time history of the wind vectors detected by the wind sensor 103, and the stability characteristics of the atmospheric boundary layer, as well as the surface roughness of the surrounding area, which is related to the stability characteristics of the boundary layer. In another embodiment, the processor 224 onboard the UAV 102 performs the back-calculation of the trajectories. Uncertainties and potential errors associated with process 400 may be reduced using concurrent and co-located wind and concentration measurements collected by sensors 103, 104 onboard the UAV 102.

Figure 5:
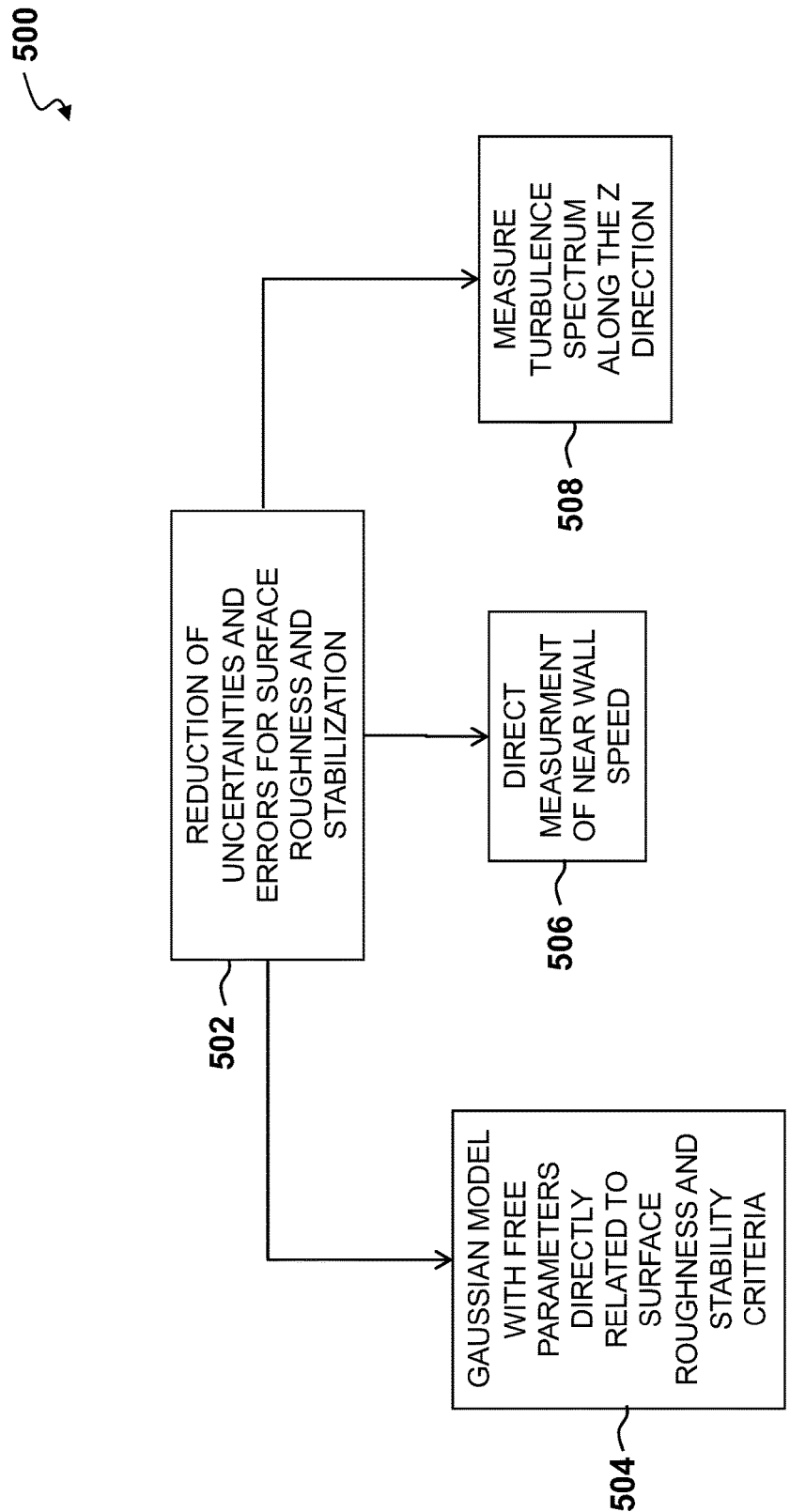
FIG. 5 shows a block diagram and process of an exemplary system in which an embodiment may be implemented.

In one embodiment, and with respect to FIG. 5, a process 500 for using concurrent and co-located wind and gas concentration measurements may be employed to directly estimate the physical parameters that describe surface roughness and stability criteria (step 502). In one embodiment, the processor 324 of FIG. 3 may execute steps of an application to fit a Gaussian profile of a model gas plume to the measured gas plume 105 of FIG. 1, with free parameters of the fit being directly related to surface roughness and stability criteria (step 504). In one embodiment, the fit may be improved by explicitly using the downwind flux plane. In another embodiment, a pair of flux planes-one upwind and one downwind of the infrastructure—may be used to determine a stream-wise gradient, thereby further constraining the free parameters of the fit.

In another embodiment, a direct measurement of near wall speed may be used to inform surface roughness and stability criteria (step 506). In one embodiment, this may be accomplished with multiple anemometers on multiple UAVs. In another embodiment, this may be accomplished by flying a trajectory purely in the Z direction, i.e., away from the ground. In yet another embodiment, a turbulence spectrum may be measured at various locations in the Z direction, which may directly inform the stability characteristics of the boundary layer (step 508).

Figure 6:
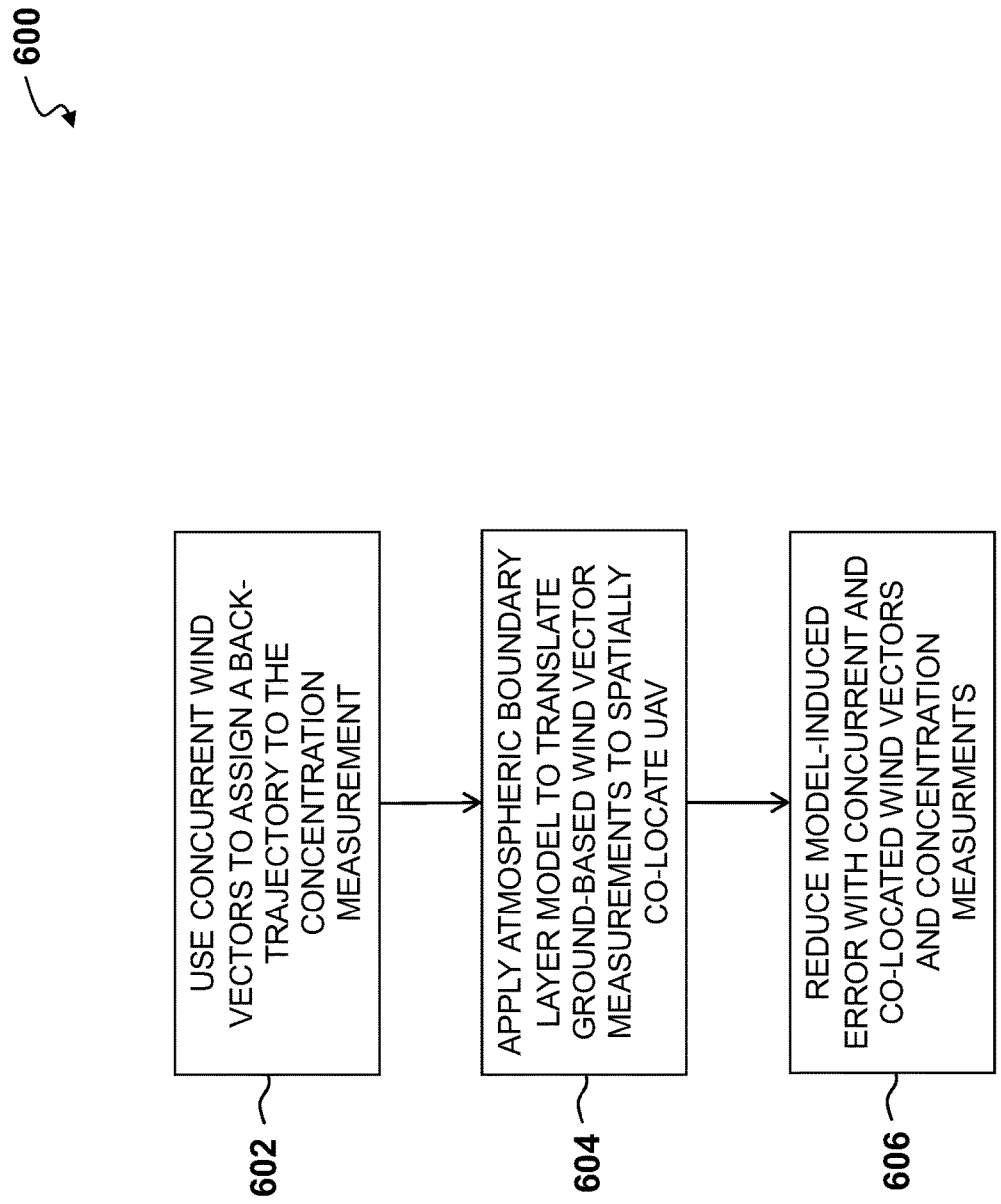
FIG. 6 shows a block diagram and process of an exemplary system in which an embodiment may be implemented.

With respect to FIG. 6, a process 600 for directly reducing the error in the localization of the gas leak with concurrent and co-located wind vectors and gas concentration measurements is presented. Concurrent wind vectors may be assigned a back-trajectory to the gas concentration measurement (step 602). Subsequently, an atmospheric boundary layer model may be applied to translate the ground-based wind vector measurements to the (x,y,z) location of the UAV 102 (step 604). Finally, a direct measurement of the wind vector concurrent and co-located with the concentration measurement may then reduce model-induced error in the localization routine (step 606).

Figure 7:
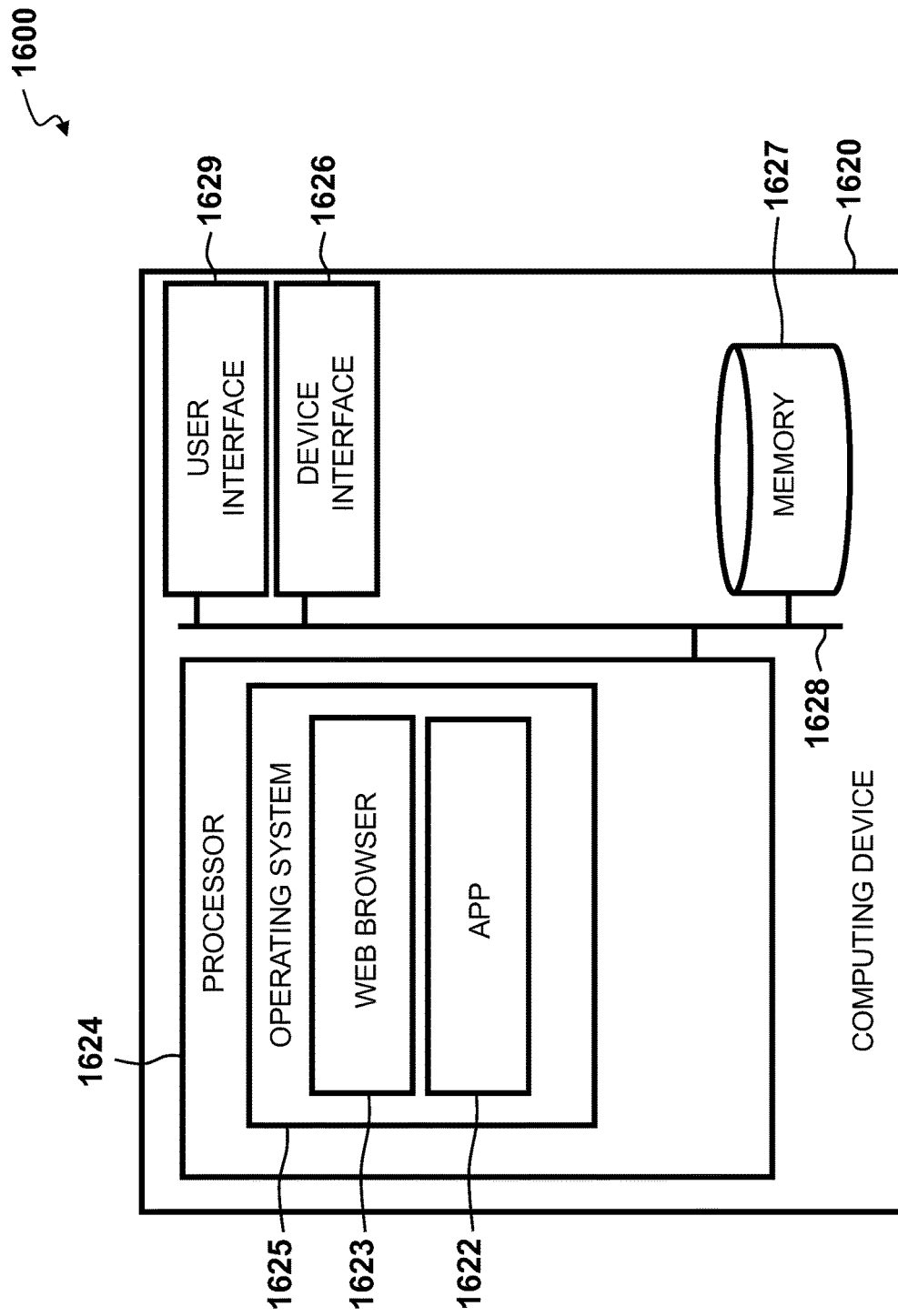
FIG. 7 illustrates an example top-level functional block diagram of a computing device embodiment, according to one embodiment.

FIG. 7 illustrates an example of a top-level functional block diagram of a computing device embodiment 1600. The example operating environment is shown as a computing device 1620 comprising a processor 1624, such as a central processing unit (CPU), addressable memory 1627, an external device interface 1626, e.g., an optional universal serial bus port and related processing, and/or an Ethernet port and related processing, and an optional user interface 1629, e.g., an array of status lights and one or more toggle switches, and/or a display, and/or a keyboard and/or a pointer-mouse system and/or a touch screen. Optionally, the addressable memory may, for example, be: flash memory, eprom, and/or a disk drive or other hard drive. These elements may be in communication with one another via a data bus 1628. In some embodiments, via an operating system 1625 such as one supporting a web browser 1623 and applications 1622, the processor 1624 may be configured to execute steps of a process establishing a communication channel and processing according to the embodiments described above.

System embodiments include computing devices such as a server computing device, a buyer computing device, and a seller computing device, each comprising a processor and addressable memory and in electronic communication with each other. The embodiments provide a server computing device that may be configured to: register one or more buyer computing devices and associate each buyer computing device with a buyer profile; register one or more seller computing devices and associate each seller computing device with a seller profile; determine search results of one or more registered buyer computing devices matching one or more buyer criteria via a seller search component. The service computing device may then transmit a message from the registered seller computing device to a registered buyer computing device from the determined search results and provide access to the registered buyer computing device of a property from the one or more properties of the registered seller via a remote access component based on the transmitted message and the associated buyer computing device; and track movement of the registered buyer computing device in the accessed property via a viewer tracking component. Accordingly, the system may facilitate the tracking of buyers by the system and sellers once they are on the property and aid in the seller's search for finding buyers for their property. The figures described below provide more details about the implementation of the devices and how they may interact with each other using the disclosed technology.

Figure 8:
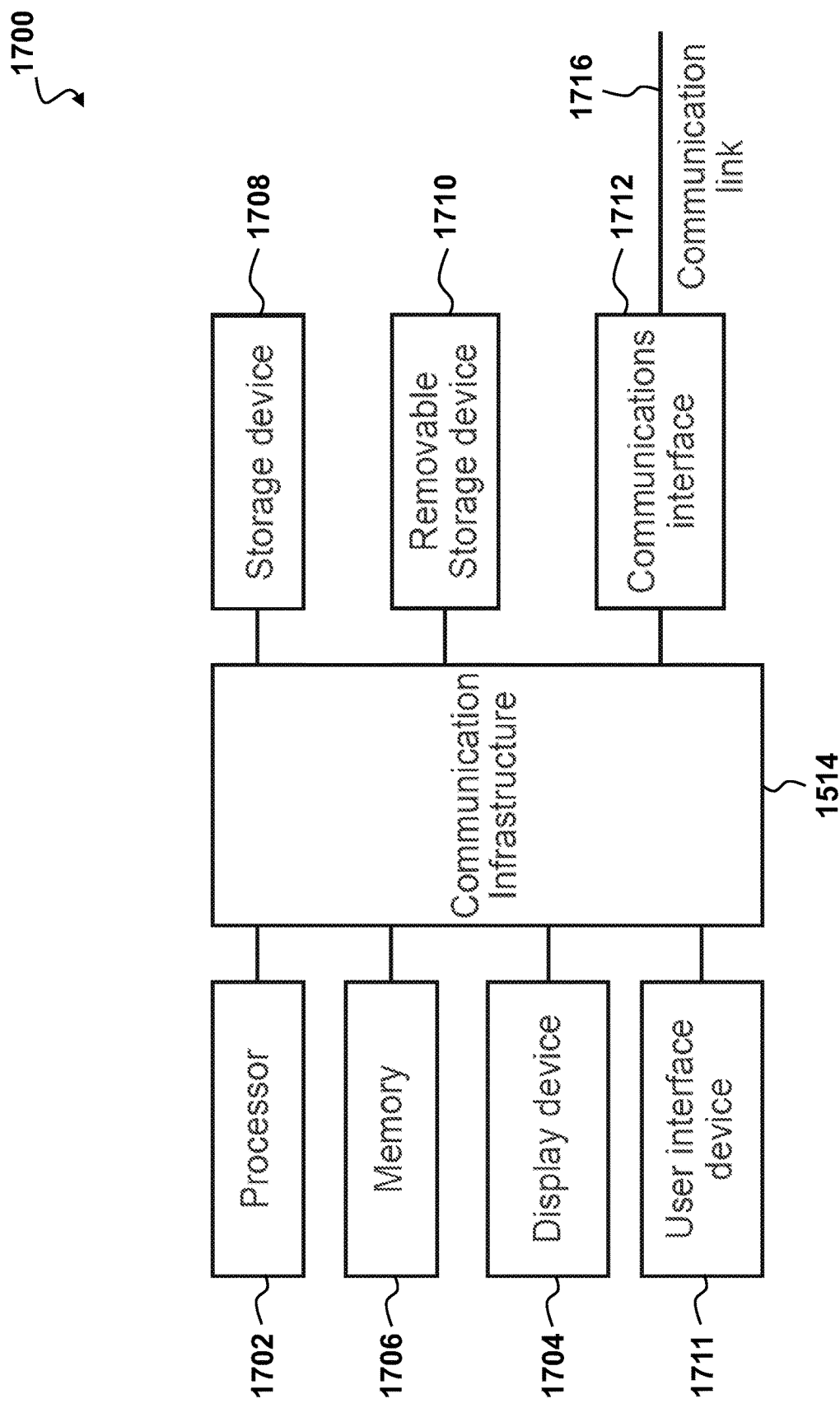
FIG. 8 shows a high-level block diagram and process of a computing system for implementing an embodiment of the system and process, according to one embodiment.

FIG. 8 is a high-level block diagram 1700 showing a computing system comprising a computer system useful for implementing an embodiment of the system and process, disclosed herein. Embodiments of the system may be implemented in different computing environments. The computer system includes one or more processors 1702, and can further include an electronic display device 1704 (e.g., for displaying graphics, text, and other data), a main memory 1706 (e.g., random access memory (RAM)), storage device 1708, a removable storage device 1710 (e.g., removable storage drive, a removable memory module, a magnetic tape drive, an optical disk drive, a computer readable medium having stored therein computer software and/or data), user interface device 1711 (e.g., keyboard, touch screen, keypad, pointing device), and a communication interface 1712 (e.g., modem, a network interface (such as an Ethernet card), a communications port, or a PCMCIA slot and card). The communication interface 1712 allows software and data to be transferred between the computer system and external devices. The system further includes a communications infrastructure 1714 (e.g., a communications bus, cross-over bar, or network) to which the aforementioned devices/modules are connected as shown.

Information transferred via communications interface 1714 may be in the form of signals such as electronic, electromagnetic, optical, or other signals capable of being received by communications interface 1714, via a communication link 1716 that carries signals and may be implemented using wire or cable, fiber optics, a phone line, a cellular/mobile phone link, an radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (i.e., computer control logic) are stored in main memory and/or secondary memory. Computer programs may also be received via a communications interface 1712. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 9:
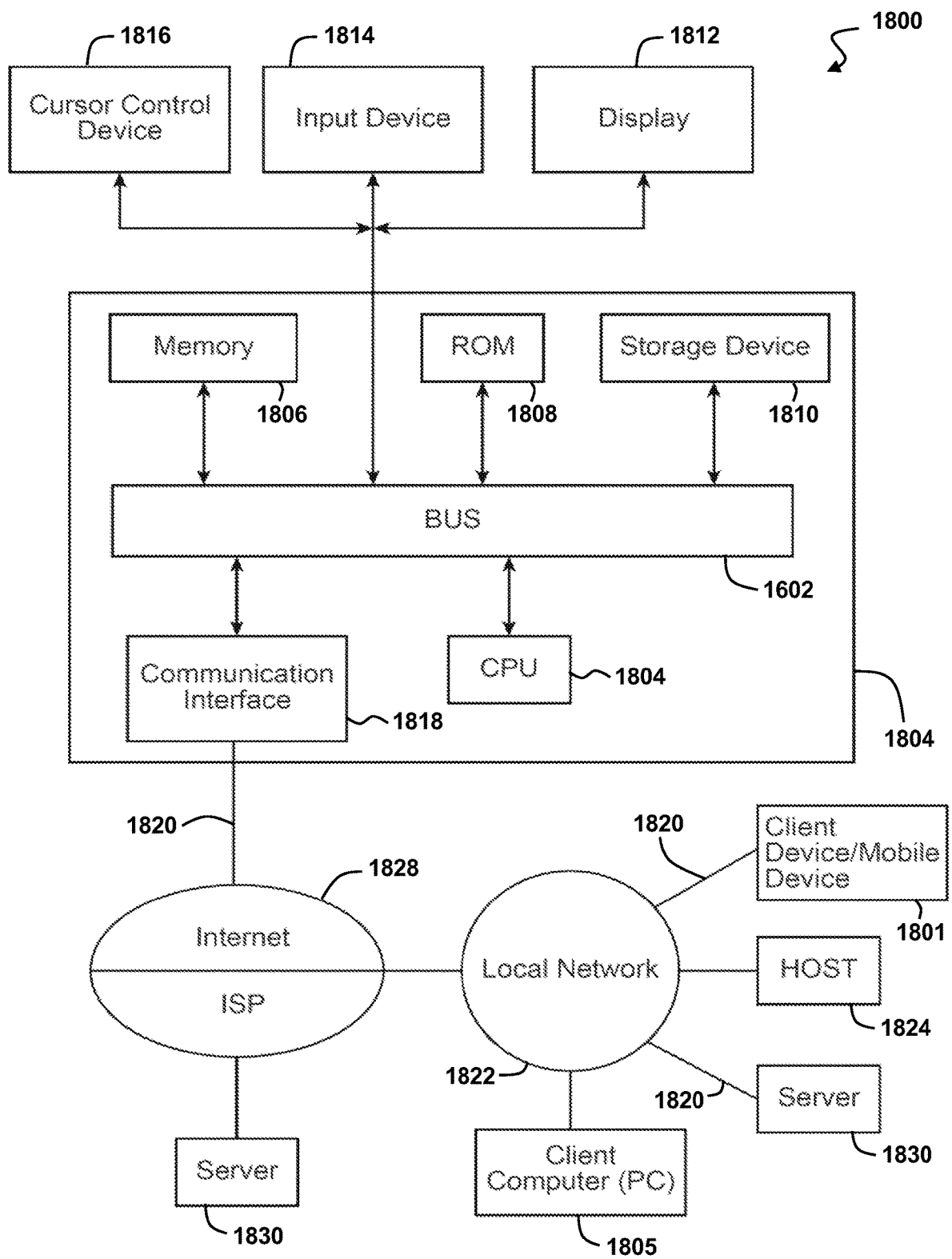
FIG. 9 shows a block diagram and process of an exemplary system in which an embodiment may be implemented, according to one embodiment.

FIG. 9 shows a block diagram of an example system 1800 in which an embodiment may be implemented. The system 1800 includes one or more client devices 1801 such as consumer electronics devices, connected to one or more server computing systems 1830. A server 1830 includes a bus 1802 or other communication mechanism for communicating information, and a processor (CPU) 1804 coupled with the bus 1802 for processing information. The server 1830 also includes a main memory 1806, such as a random access memory (RAM) or other dynamic storage device, coupled to the bus 1802 for storing information and instructions to be executed by the processor 1804. The main memory 1806 also may be used for storing temporary variables or other intermediate information during execution or instructions to be executed by the processor 1804. The server computer system 1830 further includes a read only memory (ROM) 1808 or other static storage device coupled to the bus 1802 for storing static information and instructions for the processor 1804. A storage device 1810, such as a magnetic disk or optical disk, is provided and coupled to the bus 1802 for storing information and instructions. The bus 1802 may contain, for example, thirty-two address lines for addressing video memory or main memory 1806. The bus 1802 can also include, for example, a 32-bit data bus for transferring data between and among the components, such as the CPU 1804, the main memory 1806, video memory and the storage 1810. Alternatively, multiplex data/address lines may be used instead of separate data and address lines.

The server 1830 may be coupled via the bus 1802 to a display 1812 for displaying information to a computer user. An input device 1814, including alphanumeric and other keys, is coupled to the bus 1802 for communicating information and command selections to the processor 1804. Another type or user input device comprises cursor control 1816, such as a mouse, a trackball, or cursor direction keys for communicating direction information and command selections to the processor 1804 and for controlling cursor movement on the display 1812.

According to one embodiment, the functions are performed by the processor 1804 executing one or more sequences of one or more instructions contained in the main memory 1806. Such instructions may be read into the main memory 1806 from another computer-readable medium, such as the storage device 1810. Execution of the sequences of instructions contained in the main memory 1806 causes the processor 1804 to perform the process steps described herein. One or more processors in a multi-processing arrangement may also be employed to execute the sequences of instructions contained in the main memory 1806. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium" as used herein refers to any medium that participated in providing instructions to the processor 1804 for execution. Such a medium may take many forms, including but not limited to, non-volatile media, volatile media, and transmission media. Non-volatile media includes, for example, optical or magnetic disks, such as the storage device 1810. Volatile media includes dynamic memory, such as the main memory 1806. Transmission media includes coaxial cables, copper wire and fiber optics, including the wires that comprise the bus 1802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer readable media may be involved in carrying one or more sequences of one or more instructions to the processor 1804 for execution. For example, the instructions may initially be carried on a magnetic disk of a remote computer. The remote computer can load the instructions into its dynamic memory and send the instructions over a telephone line using a modem. A modem local to the server 1830 can receive the data on the telephone line and use an infrared transmitter to convert the data to an infrared signal. An infrared detector coupled to the bus 1802 can receive the data carried in the infrared signal and place the data on the bus 1802. The bus 1802 carries the data to the main memory 1806, from which the processor 1804 retrieves and executes the instructions. The instructions received from the main memory 1806 may optionally be stored on the storage device 1810 either before or after execution by the processor 1804.

The server 1830 also includes a communication interface 1818 coupled to the bus 1802. The communication interface 1818 provides a two-way data communication coupling to a network link 1820 that is connected to the world wide packet data communication network now commonly referred to as the Internet 1828. The Internet 1828 uses electrical, electromagnetic or optical signals that carry digital data streams. The signals through the various networks and the signals on the network link 1820 and through the communication interface 1818, which carry the digital data to and from the server 1830, are exemplary forms or carrier waves transporting the information.

In another embodiment of the server 1830, interface 1818 is connected to a network 1822 via a communication link 1820. For example, the communication interface 1818 may be an integrated services digital network (ISDN) card or a modem to provide a data communication connection to a corresponding type of telephone line, which can comprise part of the network link 1820. As another example, the communication interface 1818 may be a local area network (LAN) card to provide a data communication connection to a compatible LAN. Wireless links may also be implemented. In any such implementation, the communication interface 1818 sends and receives electrical electromagnetic or optical signals that carry digital data streams representing various types of information.

The network link 1820 typically provides data communication through one or more networks to other data devices. For example, the network link 1820 may provide a connection through the local network 1822 to a host computer 1824 or to data equipment operated by an Internet Service Provider (ISP). The ISP in turn provides data communication services through the Internet 1828. The local network 1822 and the Internet 1828 both use electrical, electromagnetic or optical signals that carry digital data streams. The signals through the various networks and the signals on the network link 1820 and through the communication interface 1818, which carry the digital data to and from the server 1830, are exemplary forms or carrier waves transporting the information.

The server 1830 can send/receive messages and data, including e-mail, program code, through the network, the network link 1820 and the communication interface 1818. Further, the communication interface 1818 can comprise a USB/Tuner and the network link 1820 may be an antenna or cable for connecting the server 1830 to a cable provider, satellite provider or other terrestrial transmission system for receiving messages, data and program code from another source.

The example versions of the embodiments described herein may be implemented as logical operations in a distributed processing system such as the system 1800 including the servers 1830. The logical operations of the embodiments may be implemented as a sequence of steps executing in the server 1830, and as interconnected machine modules within the system 1800. The implementation is a matter of choice and can depend on performance of the system 1800 implementing the embodiments. As such, the logical operations constituting said example versions of the embodiments are referred to for e.g., as operations, steps or modules.

Similar to a server 1830 described above, a client device 1801 can include a processor, memory, storage device, display, input device and communication interface (e.g., e-mail interface) for connecting the client device to the Internet 1828, the ISP, or LAN 1822, for communication with the servers 1830.

The system 1800 can further include computers (e.g., personal computers, computing nodes) 1805 operating in the same manner as client devices 1801, where a user can utilize one or more computers 1805 to manage data in the server 1830.

Figure 10:
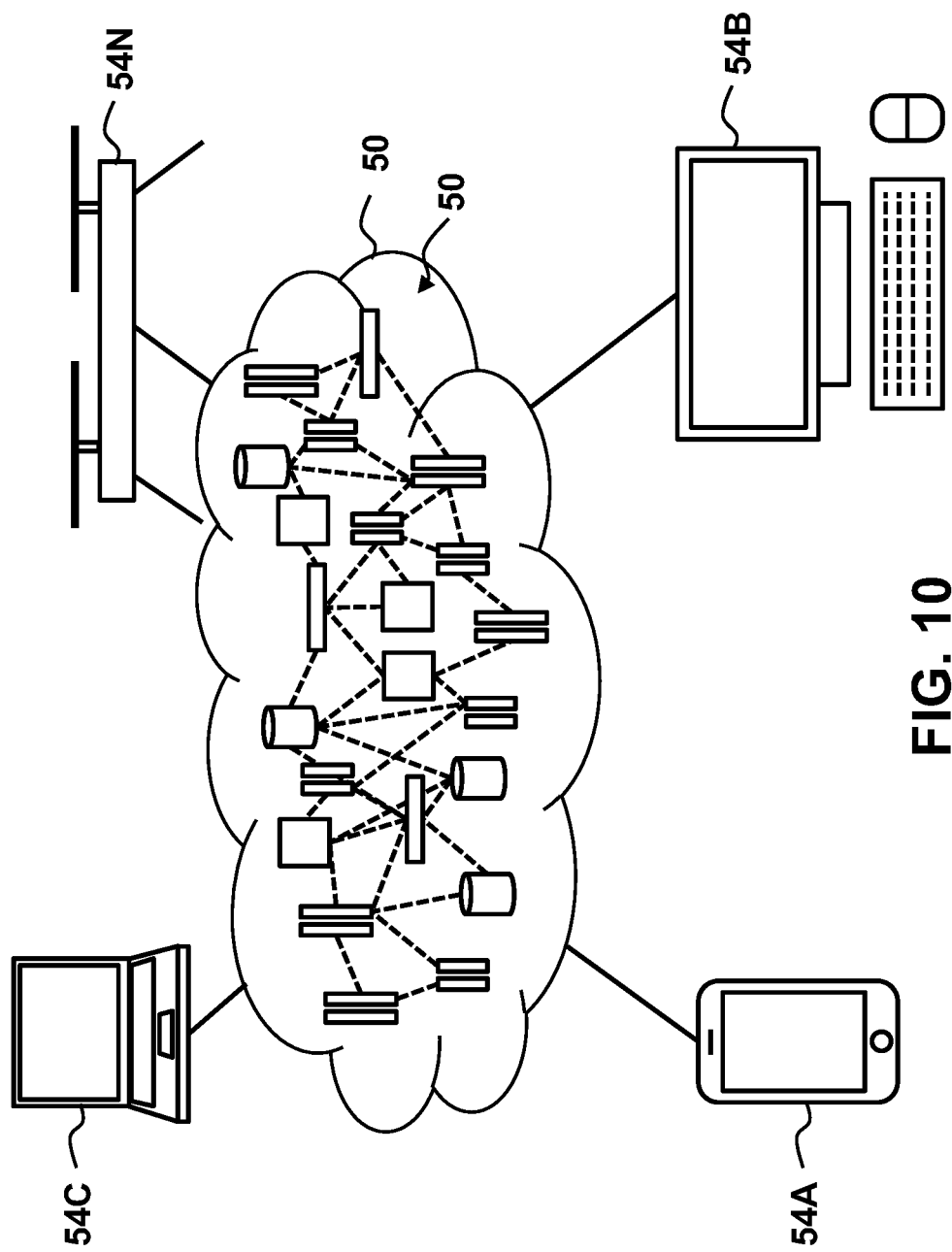
FIG. 10 depicts a cloud-computing environment for implementing an embodiment of the system and process disclosed herein, according to one embodiment.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA), smartphone, smart watch, set-top box, video game system, tablet, mobile computing device, or cellular telephone 54A, desktop computer 54B, laptop computer 54C, and/or unmanned aerial system (UAS) 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

Figure 11:
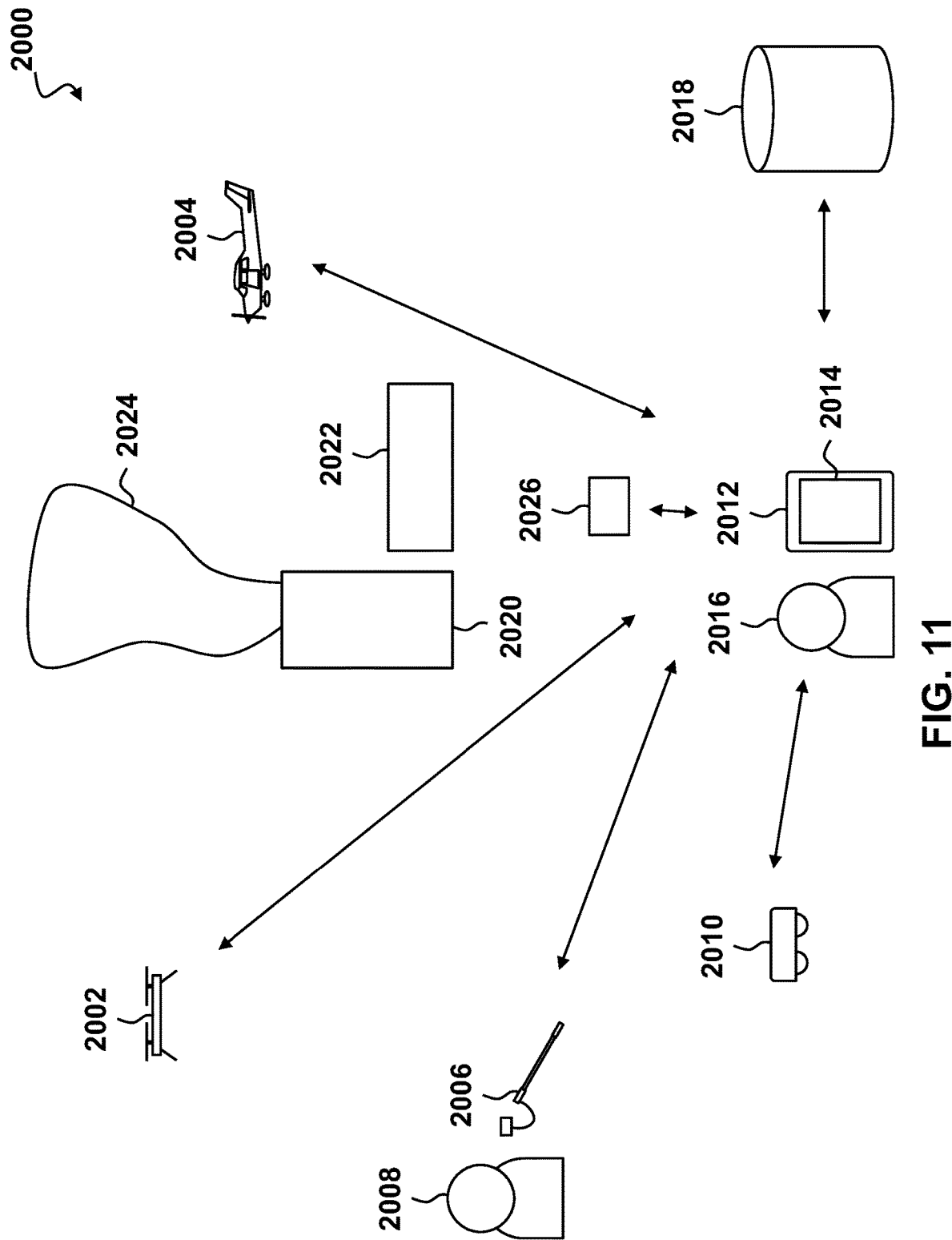
FIG. 11 depicts a system for detecting trace gasses, according to one embodiment.

FIG. 11 depicts a system 2000 for detecting trace gasses, according to one embodiment. The system may include one or more trace gas sensors located in one or more vehicles 2002, 2004, 2006, 2010. The one or more trace gas sensors may detect elevated trace gas concentrations from one or more potential gas sources 2020, 2022, such as a holding tank, pipeline, or the like. The potential gas sources 2020, 2022 may be part of a large facility, a small facility, or any location. The potential gas sources 2020, 2022 may be clustered and/or disposed distal from one another. The one or more trace gas sensors may be used to detect and quantify leaks of toxic gases, e.g., hydrogen disulfide, or environmentally damaging gases, e.g., methane, sulfur dioxide) in a variety of industrial and environmental contexts. Detection and quantification of these leaks are of interest to a variety of industrial operations, such as oil and gas, chemical production, and painting. Detection and quantification of leaks is also of value to environmental regulators for assessing compliance and for mitigating environmental and safety risks. In some embodiments, the at least one trace gas sensor may be configured to detect methane. In other embodiments, the at least one trace gas sensor may be configured to detect sulfur oxide, such as SO, SO2, SO3, S7O2, S6O2, S2O2, and the like. A trace gas leak 2024 may be present in a potential gas source 2020. The one or more trace gas sensors may be used to identify the trace gas leak 2024 and/or the source 2020 of the trace gas leak 2024 so that corrective action may be taken.

The one or more vehicles 2002, 2004, 2006, 2010 may include an unmanned aerial vehicle (UAV) 2002, an aerial vehicle 2004, a handheld device 2006, and a ground vehicle 2010. In some embodiments, the UAV 2002 may be a quadcopter or other device capable of hovering, making sharp turns, and the like. In other embodiments, the UAV 2002 may be a winged aerial vehicle capable of extended flight time between missions. The UAV 2002 may be autonomous or semi-autonomous in some embodiments. In other embodiments, the UAV 2002 may be manually controlled by a user. The aerial vehicle 2004 may be a manned vehicle in some embodiments. The handheld device 2006 may be any device having one or more trace gas sensors operated by a user 2008. In one embodiment, the handheld device 2006 may have an extension for keeping the one or more trace gas sensors at a distance from the user 2008. The ground vehicle 2010 may have wheels, tracks, and/or treads in one embodiment. In other embodiments, the ground vehicle 2010 may be a legged robot. In some embodiments, the ground vehicle 2010 may be used as a base station for one or more UAVs 2002. In some embodiments, one or more aerial devices, such as the UAV 2002, a balloon, or the like, may be tethered to the ground vehicle 2010. In some embodiments, one or more trace gas sensors may be located in one or more stationary monitoring devices 2026. The one or more stationary monitoring devices may be located proximate one or more potential gas sources 2020, 2022. In some embodiments, the one or more stationary monitoring devices may be relocated.

The one or more vehicles 2002, 2004, 2006, 2010 and/or stationary monitoring devices 2026 may transmit data including trace gas data to a ground control station (GCS) 2012. The GCS may include a display 2014 for displaying the trace gas concentrations to a GCS user 2016. The GCS user 2016 may be able to take corrective action if a gas leak 2024 is detected, such as by ordering a repair of the source 2020 of the trace gas leak. The GCS user 2016 may be able to control movement of the one or more vehicles 2002, 2004, 2006, 2010 in order to confirm a presence of a trace gas leak in some embodiments.

In some embodiments, the GCS 2012 may transmit data to a cloud server 2018. In some embodiments, the cloud server 2018 may perform additional processing on the data. In some embodiments, the cloud server 2018 may provide third party data to the GCS 2012, such as wind speed, temperature, pressure, weather data, or the like.

It is contemplated that various combinations and/or sub-combinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention is herein disclosed by way of examples and should not be limited by the particular disclosed embodiments described above.

What is claimed is:

1. A system for determining a gas leak rate, the system comprising:
   a trace gas sensor configured to measure a plurality of gas point concentrations at a plurality of locations;
   a wind sensor configured to determine a discrete wind vector at the plurality of locations; and
   a processor configured to: determine a leak rate of a gas plume based on the measured gas point concentration and the discrete wind vector; and determine a flux rate of gas in a surface integral on a flux plane, by multiplying the surface integral by a freestream velocity, wherein the freestream velocity comprises a velocity with which the flux plane is moving through the gas plume.

2. The system of claim 1, wherein the discrete wind vector is measured proximate a location where the gas point concentration is measured.

3. The system of claim 1, wherein the discrete wind vector is measured proximate a same time the gas point concentration is measured.

4. The system of claim 1, wherein the discrete wind vector is measured at a location where the gas point concentration is measured and at a same time the gas point concentration is measured.

5. The system of claim 1, wherein the system is configured to fly along a flight plan, and the trace gas sensor and the wind sensor measure the gas point concentrations and wind vectors respectively while the system flies the flight plan.

6. The system of claim 5, further comprising:
   an unmanned aerial vehicle (UAV) flying along the flight plan, wherein the trace gas sensor and the wind sensor are disposed on the UAV.

7. The system of claim 5, wherein the flight plan captures a cross section of the gas plume based on a detected elevated trace gas concentration.

8. A system for determining a gas leak rate, the system comprising:
   a trace gas sensor configured to measure a plurality of gas point concentrations at a plurality of locations;
   a wind sensor configured to determine a discrete wind vector at the plurality of locations; and
   a processor configured to: determine a leak rate of a gas plume based on the measured gas point concentration and the discrete wind vector; determine an elevated gas point concentration from among the plurality of gas point concentrations; and determine the leak rate of the gas plume by determining a flux rate of gas in a surface integral on a flux plane of the gas plume based on the elevated gas point concentration.

9. The system of claim 8, wherein the processor is further configured to localize a gas leak of the gas plume based on the flux rate and the discrete wind vector.

10. The system of claim 8, wherein the discrete wind vector is measured proximate a location where the gas point concentration is measured.

11. The system of claim 8, wherein the discrete wind vector is measured proximate a same time the gas point concentration is measured.

12. The system of claim 8, wherein the discrete wind vector is measured at a location where the gas point concentration is measured and at a same time the gas point concentration is measured.

13. The system of claim 8, wherein the system is configured to fly along a flight plan, and the trace gas sensor and the wind sensor measure the gas point concentrations and wind vectors respectively while the system flies the flight plan.

14. The system of claim 13, further comprising:
   an unmanned aerial vehicle (UAV) flying along the flight plan, wherein the trace gas sensor and the wind sensor are disposed on the UAV.

15. The system of claim 13, wherein the flight plan captures a cross section of the gas plume based on the detected elevated trace gas concentration.

* * * * *